United States Patent
Della Valle et al.

(10) Patent No.: US 9,399,031 B2
(45) Date of Patent: Jul. 26, 2016

(54) COMBINED USE OF AMIDES OF MONO- AND DICARBOXYLIC ACIDS AND SILYMARIN IN THE TREATMENT OF RENAL DISEASES

(71) Applicant: Epitech Group S.r.l., Milan (IT)

(72) Inventors: Francesco Della Valle, Milan (IT); Maria Federica Della Valle, Milan (IT); Gabriele Marcolongo, Milan (IT); Salvatore Cuzzocrea, Milan (IT)

(73) Assignee: Epitech Group S.r.l., Milan (IT)

( * ) Notice: Subject to any disclaimer, the term of this patent is extended or adjusted under 35 U.S.C. 154(b) by 91 days.

(21) Appl. No.: 14/323,673

(22) Filed: Jul. 3, 2014

(65) Prior Publication Data

US 2015/0011617 A1 Jan. 8, 2015

(30) Foreign Application Priority Data

Jul. 5, 2013 (IT) .............................. MI2013A1132

(51) Int. Cl.
| | | |
|---|---|---|
| *A61K 31/357* | (2006.01) | |
| *A61K 31/164* | (2006.01) | |
| *A61K 45/06* | (2006.01) | |
| *A61K 36/28* | (2006.01) | |
| *A61K 9/00* | (2006.01) | |

(52) U.S. Cl.
CPC .................. *A61K 31/357* (2013.01); *A61K 9/00* (2013.01); *A61K 31/164* (2013.01); *A61K 36/28* (2013.01); *A61K 45/06* (2013.01)

(58) Field of Classification Search
CPC ............................ A61K 31/357; A61K 31/164
USPC ......................................................... 514/452
See application file for complete search history.

(56) References Cited

FOREIGN PATENT DOCUMENTS

EP 2 444 078 A1 4/2012

OTHER PUBLICATIONS

H. Senturk et al. "Silymarin Attenuates the Renal Ischemia/Reperfusion Injury-Induced Morphological Changes in the Rat Kidney." World J. Urol., vol. 26, pp. 401-407, 2008.
F. Turgut et al., "Antioxidant and Protective Effects of Silymarin on Ischemia and Reperfusion Injury in the Kidney Tissues of Rats." Int. Urol. Nephrol., vol. 40, pp. 453-460, 2008.
F. Shahbazi et al., "Potential Renoprotective Effects of Silymarin Against Nephrotoxic Drugs: A Review of Literature." J. Pharm. Pharmaceut. Sci., vol. 15, No. 1, pp. 112-123, 2012.

*Primary Examiner* — Raymond Henley, III
(74) *Attorney, Agent, or Firm* — Blank Rome LLP

(57) ABSTRACT

A therapy for renal diseases characterized by alterations of the kidney function, such as Chronic Kidney Disease (CKD), acute and chronic renal impairment, and renal diseases that develop in diabetic patients or in patients who underwent an anticancer chemotherapic treatment with a platinum derivative. The invention is a combination of compounds selected from mono- or diamide of a C12-C20 monocarboxylic acid, saturated or monounsaturated, or a C4-C14 dicarboxylic acid, saturated or monounsaturated, with an aminoalkanol, and compounds selected from Silymarin, derivatives thereof or conjugates or complexes thereof, for use in the treatment of renal diseases. The mono- or diamide of a C12-C20 monocarboxylic acid, saturated or monounsaturated, or of a C4-C14 dicarboxylic acid, saturated or monounsaturated, with an aminoalkanol and said Silymarin, derivatives thereof or conjugates or complexes thereof are formulated for a separate, sequential, concomitant administration or in admixture, also in a co-micronized or co-ultra-micronized form.

16 Claims, 2 Drawing Sheets

COMBINED USE OF AMIDES OF MONO- AND DICARBOXYLIC ACIDS AND SILYMARIN IN THE TREATMENT OF RENAL DISEASES

BACKGROUND OF THE INVENTION

1. Field of the Invention

The present invention relates to a therapy of renal diseases characterized by alterations of the kidney function, such as Chronic Kidney Disease (CKD), acute and chronic renal impairment, particularly, but not limited to, renal diseases that develop in diabetic patients or who underwent an anti-cancer chemotherapic treatment with a platinum derivative, and more generally, cytotoxic drugs at the kidney level for treating neoplastic diseases.

2. Description of the Related Art

Chronic Kidney Disease and the resulting renal impairment are extremely frequent diseases, even if they are under-diagnosed; in fact, it is estimated that they affect 17% of adult population.

The most frequent renal disease is characterized by an injury to the renal glomeruli.

Renal diseases may be hereditary or acquired; particularly, the acquired diseases may have a different etiology:

Immunologic, such as Goodpastures' syndrome, Lupus nephritis, and Immunoglobulins A nephropathy. In the case of the immunologically-mediated renal disease, its cause is the presence of a strong antigenic stimulus that elicits an immune reaction;

Dismetabolic, and particularly Diabetic nephropathy, one of the most frequent causes for chronic renal impairment. Prevalence is 20-30% in patients affected by type 1 Diabetes and about 10% in cases of type 2 Diabetes. It is a deceitful disease, since it is characterized by a particularly slow outbreak (up to 20-30 years from Diabetes outbreak) and essentially asymptomatic for a long period; it initially exhibits with a microalbuminuria (amount of albumin in the urine ranging between 30 and 300 mg/l), which slowly evolves toward macroalbuminuria, indicative of an established nephropathy (amount of albumin in the urine above 300 mg/l, until reaching values of 3 g in the 24 hours);

haemodynamic, from arterial hypertension. An alteration in the mechanisms of the kidney blood stream pressure leads, over time, to a decrease in the kidney filtering ability;

ischemic. Renal ischemia is the pathogenetic event most frequently involved in the acute renal impairment and the resulting tubular necrosis, in both native and transplanted kidneys;

toxic. Many of the clinically significant drugs (cytotoxic, chemotherapic agents, non-steroideal anti-inflammatory drugs, corticosteroid therapies, etc.) and several chemicals (such as radiologic contrast means, solvents, etc.) cause nephrotoxicity, which is able to very frequently cause a renal parenchyma inflammation and both transient and chronic functional impairment.

Also in veterinary medicine, renal diseases which will evolve toward a chronic renal impairment compose a important clinical niche, representing the second cause of death in dogs, after tumoral diseases, and the first cause of death in older cats. From an etiology viewpoint, the causes determining the progressive and irreversible loss of functionality of nephrons in small animals were precisely classified (Squires et al, 1998) in:

Degenerative: interstitial chronic nephritis; kidney infarction

Autoimmune: glomerulonephritis from anti-glomerular Abs

Metabolic: Diabetes; hyperthyroidism (cat); hypercalcemia

Neoplastic: renal lymphomas and carcinomas

Idiopathic: amyloidosis; idiopathic-based glomerulonephrites

Infective: bacterial pielonephrites; Lyme nephropathy (Borreliosis)

Immuno-mediated: glomerulonephritis from immuno-complexes

Toxic: nephrotoxic drugs (e.g. cisplatin, amino glycosides, NSAIDs)

Traumatic: bladder and urethra rupture.

One of the major targets of nephrology is, firstly, to understand the mechanism regulating the passage from an acute kidney injury to fibrotic Chronic Kidney Disease, since, once fibrogenesis has started, it may be currently very difficult to intervene on the fibrotic process; in any case, the target to stop or at least slow down the progression of Chronic Kidney Disease remains extremely relevant, in view that such a disease also constitutes an important risk factor for cardiovascular diseases. In this regard, many studies are under way to precisely understand the most relevant outbreak mechanisms, aiming to prevent those phenomena determining the irreversibility of this disease.

In spite of the number of new acquisitions on the pathogenic mechanisms involved in the development of the renal diseases, still no satisfactory therapeutic options exist for controlling these conditions.

Palmitoylethanolamide (PEA) is the progenitor of a family of N-acylamides called ALIAmides: a class of endogenous lipid molecules capable of normalizing the activity of immune cells by a local antagonist-type mechanism. Clinically, oral intake of PEA-containing products is able to improve neuropathic symptoms related to the peripheral neuropathy, while promoting a functional recovery of motor conduction velocity. PEA, at an experimental level, has shown to be efficient also in dismetabolic neuropathies, particularly, the administration thereof in an animal model of diabetes by streptozotocin suppresses allodynia and induces a partial body weight recovery and an increase in blood insulin levels.

Similarly to PEA, certain N-acylamides, generally formed by monoethanolamine and saturated and not saturated dicarboxylic fatty acids, not being per se physiologic, yet capable of forming, in their catabolism, substance that are found physiologically in the mammal's body, while not causing any build-up and/or toxicity, showed to be capable of causing pharmacological effects that are similar to the progenitor PEA.

The activity of PEA and other ALIAmides in the treatment of renal diseases has been already described by the Applicant in the European Patent Application Publication No. 2444078 A1, published on Apr. 25, 2012.

Silymarin is an extract of the plant *Silybum marianum*, also known as milk thistle, the activity of which in the treatment of liver diseases is known.

SUMMARY OF THE INVENTION

We have now surprisingly found that the combined use of some molecules belonging to the class of amides between an amine alcohol and a mono- or dicarboxilic acid and Silymarin involves a marked synergic effect in the treatment of renal diseases, even when the above-mentioned amide is administered in doses that per se are not therapeutically efficient. Particularly, it has been noticed that specific combinations of palmitoylethanolamide (PEA) and Silymarin showed a considerably synergic activity against said diseases.

Therefore, it is a first object of the present invention an amide of a C12-C20 monocarboxylic acid, saturated or monounsaturated, or a mono- or diamide of a C4-C14 dicarboxylic acid, saturated or monounsaturated, with an aminoalkanol (generally also referred to as ALIAamide), in combination with Silymarin, derivatives thereof or conjugates or complexes thereof with suitable carriers, for use in a therapy of renal diseases characterized by alterations of kidney function, such as CKD, acute or chronic renal impairment, particularly, but not limited to, renal diseases caused by dysmetabolic diseases or toxic agents.

It is a further object of the invention palmitoylethanolamide (PEA) in combination with Silymarin for use in the treatment of renal diseases, wherein PEA is preferably in a micronized form or in an ultra-micronized form, wherein the combination of PEA and Silymarin may also be obtained in a co-micronized and/or co-ultra-micronized form.

DETAILED DESCRIPTION OF THE INVENTION

Figure 1:
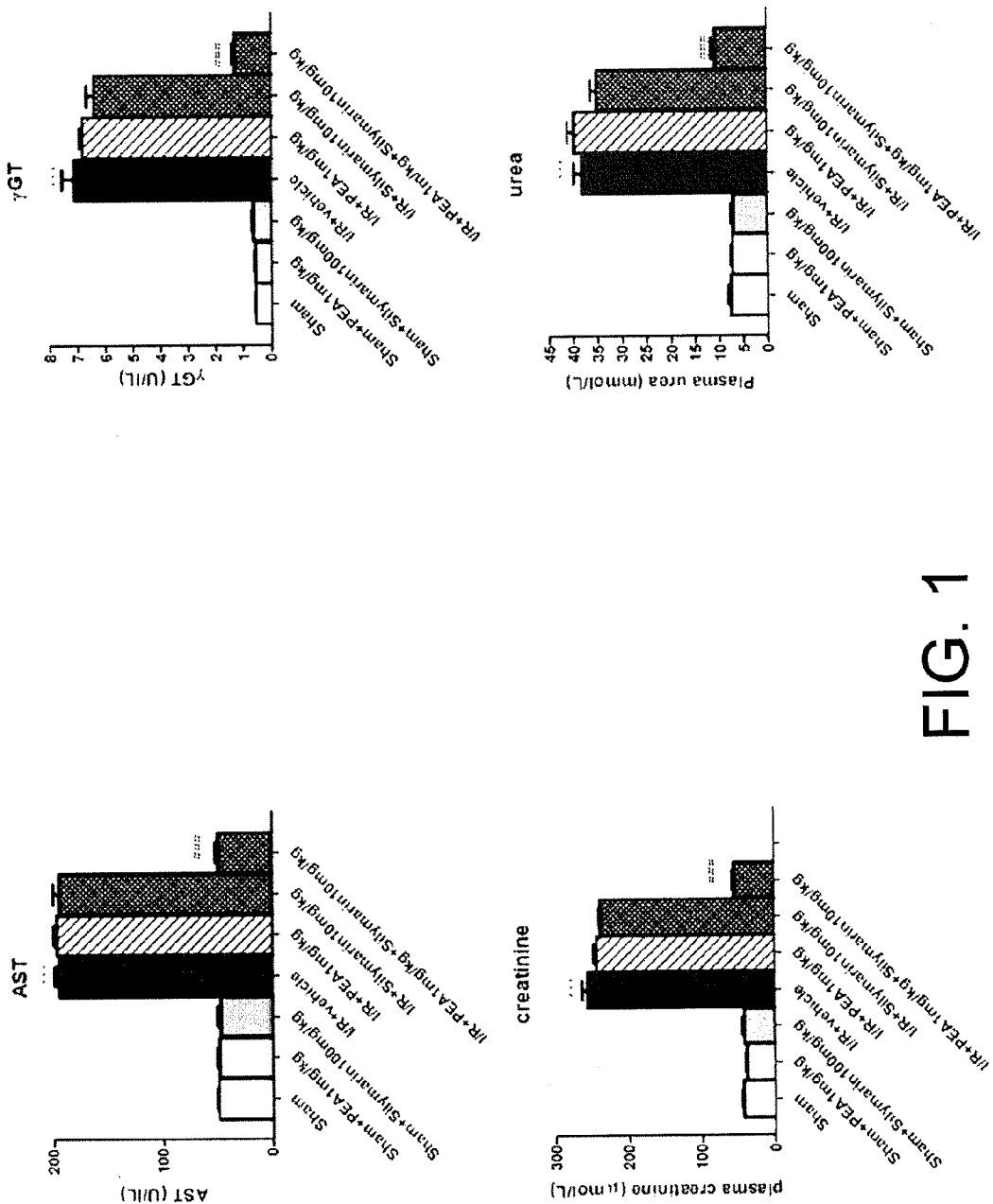
FIG. 1 represents block diagrams in which plasma concentration of AST, γGT, creatinine, and urea at 6 hours post-reperfusion are reported, respectively, in mice treated with the combination of active ingredients of the invention compared to the two active ingredients isolated and with the control.

The present invention is based on the surprising finding that the exogenous administration of an amide of a C12-C20 monocarboxylic acid, saturated or monounsaturated, or a mono- or diamide of a C4-C14 dicarboxylic acid, saturated or monounsaturated, with an aminoalkanol, particularly the administration of Palmitoylethanolamide, preferably in a micronized form (PEAm) or in an ultra-micronized form (PEAum), in combination with Silymarin, derivatives thereof or conjugates or complexes thereof with suitable carriers, wherein said active ingredients may be in co-micronized and/or co-ultra-micronized form, is able to substantially improve, with a synergic effect, the renal function in a mammal afflicted with renal impairment, even when said amide is administered at a per se not therapeutically efficient dosage.

In an embodiment of the invention, said C12-C20 monocarboxylic acid, saturated or monounsaturated, is selected from palmitic acid, stearic acid and oleic acid.

In an embodiment of the invention, said C4-C14 dicarboxylic acid, saturated or monounsaturated, is selected from fumaric acid, azelaic acid and trans-traumatic acid.

Palmitoylethanolamide is a commercially available product, which may be prepared by conventional methods, well known to those skilled in the art, such as those providing for a reaction between ethanolamine, optionally in a protected form, and palmitic acid under suitable condensation conditions, which may also provide for the use of condensing agents. The other amides that may be encompassed in the formulation of the present invention may be synthetized in a completely similar manner, by using methods well known to those skilled in the art.

By the term "PEA in a micronized form" or "PEAm" is meant a palmitoylethanolamide in which at least 94% or at least 95% or about 96% of the particles has a size of less than 10 microns and preferably at least 77% or at least 78% or about 80% of the particles has a size of less than 6 microns. PEAm may be prepared according to the teachings of the European patent No. EP 1 207 870 B1.

By the term "PEA in an ultra-micronized form" or "PEAum" is meant a palmitoylethanolamide in which at least 97% or at least 98% or at least 99% or about 99.9% of the particles has dimensions of less than 6 microns and preferably at least 57% or at least 58% or at least 59% or about 59.6% of the particles has dimensions of less than 2 microns. PEAum may be prepared according to the teachings of PCT Publication No. WO 2011/027373 A1.

By the phrase "Silymarin, derivatives thereof or conjugates or complexes thereof with suitable carriers" is meant, in a non-limiting way, a compound or a mixture of compounds selected from a total or partial extract of the plant *Silybum marianum*, Silibinin (2R,3R)-3,5,7-trihydroxy-2-[(2R,3R)-3-(4-hydroxy-3-methoxyphenyl)-2-(hydroxymethyl)-2,3-dihydrobenzo[b][1,4]dioxine-6-il]chroman-4-on, Silibinin disodium dihydrogensuccinate, Silypide (complex between Silymarin and phosphatidylcholine), the inclusion complexes of Silymarin in β-cyclodextrins (preferably hydroxypropyl-β-cyclodextrin and methylated β-cyclodextrin), and Silibinin glycosides.

Silymarin is an extract from the seeds of *Silybum marianum*, the pharmacological activity of which relating to the liver diseases is widely known.

Silibinin, or Silybin, is the main component of Silymarin. Silymarin further comprises Silydianin and Silycristin (1:3 ratio with respect to Silybin) and, to a lower extent, the isomers isosilybin, isosilycristin and silandrin.

The present invention relates to an amide of a C12-C20 monocarboxylic acid, saturated or monounsaturated, or a mono- or diamide of a C4-C14 dicarboxylic acid, saturated or monounsaturated, with an aminoalkanol (generally also referred to as ALIAmide), in combination with Silymarin, derivatives thereof or conjugates or complexes thereof with suitable carriers, for use in the treatment of renal diseases characterized by alterations of kidney function, such as CKD, acute and chronic renal impairment, particularly, but not limited to, renal diseases caused by dysmetabolic diseases or toxic agents.

In an embodiment, said ALIAmide is PEA.

In an embodiment, PEA is used in a micronized form (PEAm).

In a different embodiment, PEA is used in an ultra-micronized form (PEAum), alone or in admixture with PEAm.

Silymarin, derivatives thereof or conjugates or complexes thereof is administered in a weight ratio ranging between 15:1 and 5:1, preferably about 10:1, with respect to ALIAmide.

The administration of one or more ALIAmides with at least one of Silymarin, derivatives thereof or conjugates or complexes thereof is provided for, in which the combined use provides for a separate, sequential, concomitant administration or in admixture.

The at least one ALIAmide and Silymarin, derivatives thereof or conjugates or complexes thereof may be used in a co-micronized and/or co-ultra-micronized form.

Pharmacological Activity of the Compounds of the Invention

Experimental Renal Ischemia/Reperfusion Model

After being anesthesized with sodium pentobarbital (50 mg/kg i.p.), mice were placed on a heated mat to keep their body temperature at 37° C. during surgery. After a laparatomy, mice were subjected to bilateral renal ischemia during 30 minutes, during which renal arteries and veins were occluded by microaneurysm clamps. The ischemia time selected was based on the time capable of maximizing the reproducibility of the renal function unbalance, while minimizing animal death. After removing renal clamps, kidneys were observed during additional 5 minutes to confirm complete reperfusion, and subsequently 1 ml saline was injected into the abdomen and incision was sutured. Mice were kept under a heating lamp for recovery, then brought back to their cages, where they have been kept in observation status for 6 hours. Control mice underwent the same intervention, but without placing microaneurysm clamps.

Biochemical Parameter Measurement

At the completion of the reperfusion period, 1 mL blood samples were taken by heart puncture. The samples were centrifuged (6000 rpm during 3 minutes) to separate plasma. All plasma samples were analyzed for assessing the biochemical parameters within 24 hours post-withdrawal. Plasma concentrations of urea and creatinine were measured as indicators of the impaired glomerular function. Plasma concentrations of γ-glutamyl transferase (GT) and aspartate aminotransferase (AST) were used as indicators of renal reperfusion injury.

Determination of Myeloperoxydase Activity

Myeloperoxydase (MPO) activity in kidneys was used as an indicator of polymorphonuclear cell infiltration (PMN). Briefly, at the end of the experiments, kidney tissue was weighted and homogenized in a solution containing 0.5% w/v of hexadecyl trimethylammonium bromide dissolved in 10 mmol/l of a potassium phosphate buffer (pH 7.4) and centrifuged during 30 minutes at 20,000 rpm at 4° C. A portion of supernatant was removed and added to a reaction mixture containing 1.6 mmol/l tetramethylbenzidine and 0.1 mmol/l hydrogen peroxide. Absorbance change rate was spectrometrically measured at 650 nm. MPO activity was defined as the amount of enzyme necessary to degrade 1 mmol hydrogen peroxide at 37° C., and it was expressed in U/g wet tissue.

Determination of Malondialdehyde Levels Malondialdehyde (MDA) levels in kidneys were determined as an indicator of lipid peroxidation.

Briefly, kidney tissue was weighted and homogenized in a 1.15% w/v KCl solution. A 100 ml portion of the homogenate was then removed and added to a reaction mixture containing 200 ml lauryl sulphate 8.1% w/v, 1.5 ml acetic acid 20% v/v (pH 3.5), 1.5 ml thiobarbituric acid 0.8% w/v, and 700 ml distilled water. Samples were boiled during 1 hour at 95° C. and centrifuged at 3000 rpm during 10 minutes. Supernatant absorbance was spectrometrically measured at 532 nm. MDA levels were expressed as μM/100 mg wet tissue.

Optical Microscopy

Kidney tissue was taken after 6 hours post-reperfusion, fixed during 1 week in a buffered formaldehyde solution (10% in phosphate buffer saline) at room temperature, dried over ethanol and embedded in Paraplast (Sherwood Medical, Mahwah, N.J.). Tissue sections (7 micron thickness) were deparaffinized with xylene, stained with hematoxylin/eosin, and observed under an optical microscope (Zeiss Milan, Italy). For the histological assessment, the renal sections were prepared as described before and used for the assessment of renal reperfusion injury (Patel et al., 2004). Briefly, 100 intersections for each kidney were examined, and each tubular profile comprising an intersection was assigned a to 3 score: 0, normal histology; 1, tubular cell swelling, brush border loss, nuclear condensation, with up to ⅓ of tubular profile showing a tubular loss; 2, as for score 1, but more than ⅓ and less than ⅔ of tubular profile showing a nuclear loss; 3, more than ⅔ of tubular profile showing a cell loss. Total scoring for each kidney was calculated by the sum of all the 100 scores, with a maximum score of 300. All histological studies were carried out in a blind manner.

Statistical Analysis

Figure 2:
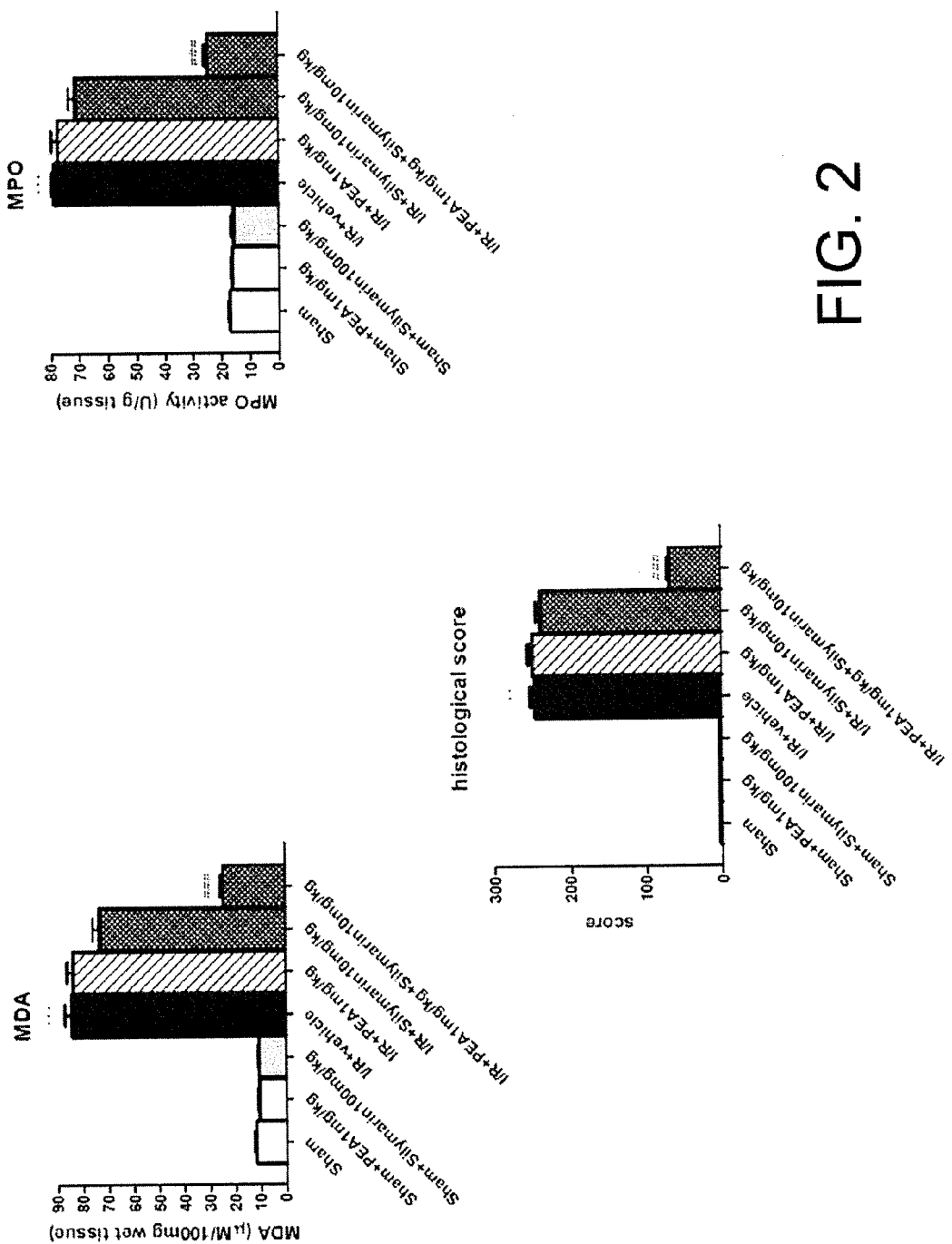
FIG. 2 represents block diagrams in which the MDA levels, MPO renal activity, and histologic assessment of renal tissues at 6 hours post-reperfusion are reported, respectively, in mice treated with the combination of active ingredients of the invention compared to the two active ingredients isolated and with the control.

All the values in FIGS. 1 and 2 and throughout the text are expressed as the mean±standard error of the mean (SEM) of N observations. N represents the number of animals under study. In the histology experiments, numbers are representative of at least 3 experiments performed on different days. The results were analyzed by one-way ANOVA, followed by a post-hoc Bonferroni's test for multiple comparison.

* * *

The results shown in FIGS. 1 and 2 clearly show that the use an ALIAamide, particularly Palmitoylethanolamide (PEA), in combination with Silymarin, gives rise to a relevant synergic effect in improving functional and tissue parameters for kidneys in mammals afflicted with kidney failure, therefore it can be used successfully in the treatment of renal diseases. A similar synergic effect can be achieved with Silymarin derivatives or conjugates of complexes thereof.

As it can be noticed by the diagrams set forth for the various parameters measured, neither Silymarin alone nor PEA alone, when used at the same doses as in the combination, showed an improvement effect when compared to the carrier alone. Vice versa, the combination thereof tends to normalize the observed parameters.

The most relevant and unexpected observation is that PEA performs its activity in combination with Silymarin at per se not therapeutically efficient doses.

Therefore, the compounds of the invention can be used, in both humans and pets, in the treatment of renal diseases.

Such diseases are preferably selected from:
CKD: Chronic Kidney Disease
Diabetic nephropathy
Nephro-angio-sclerosis
Pielonephritis
Polycystic kidney disease (polycystic kidney)
Alport's syndrome
Lesch-Nyham's syndrome
Goodpastures' syndrome
Lupus nephritis
Immunoglobulins A nephropathy
Tubular necrosis
Glomerulonephritis
Urethral stenosis
Iatrogenic nephropathies (from NSADs, cytotoxic drugs, Lithium, antibiotics, Cyclosporine, etc.)
Nephropathies after radiation therapy
Nephropathies in the elderly.

Therefore, the compounds of the invention may be formulated for an oral, buccal, parenteral, rectal, or transdermal administration.

PEA may be preferably formulated for an oral administration.

For oral administration, the pharmaceutical compositions may be found, for example, in the form of tablets or capsules prepared in a conventional manner with pharmaceutically acceptable excipients, such as binders (for example, pre-gelatinized corn starch, polyvinylpyrrolidone or hydroxypropyl methyl cellulose); filling agents (for example, lactose, microcrystalline cellulose, or calcium hydrogen phosphate); lubricants (for example, magnesium stearate, talc, or silica); disintegrants (for example, potato starch or sodium starch glycolate); or inhibiting agents (for example, sodium lauryl sulphate). Tablets may be coated by methods that are well known in the art. Liquid preparations for oral administration may by, for example, in the form of solutions, syrups or suspensions, or they may be in the form of lyophilized products to be reconstituted, before use, with water or other suitable vehicles. Such liquid preparations may be prepared by conventional methods with pharmaceutically acceptable additives, such as suspension agents (for example, sorbitol syrup, cellulose derivatives, or edible hydrogenated fats); emulsifying agents (for example, lecithin or acacia); non-aqueous vehicles (for example, almond oil, oily esters, ethyl alcohol, or fractionated vegetable oils); and preservatives (for example, methyl- or propyl-p-hydroxybenzoates or sorbic acid). The preparation may also suitably contain flavors, colorants and sweetening agents.

Preparations for oral administration may be suitably formulated to allow the controlled release of the active ingredients(s).

For buccal administration, the compositions may be in the form of tablets or pills formulated in a conventional manner, suitable to an absorption at the buccal mucosa. Typical buccal formulations are the tablets or granulates for a sub-lingual administration.

The compounds of the invention may be formulated for a parenteral administration by injection. The formulations for injections may be in the form of a single dose, for example, in vials, with a preservative added. The compositions may be in such a form as suspensions, solutions or emulsions in oily or aqueous vehicles, and the can contain agents from handbook, such as suspension agents, stabilizers and/or dispersing agents. Alternatively, the active ingredient may be in the form of a powder to be reconstituted, before use, with a suitable vehicle, for example, sterile water.

According to the present invention, the compounds of the invention may also be formulated for rectal compositions, such as suppositories or retention enema, for example, containing the base components of typical suppositories, such as cocoa butter or other glycerides.

In addition to the compositions described above, the compounds of the invention may also be formulated as depot preparations. Such long-acting formulations may be administered by an implant (for example, subcutaneously, transcutaneously, or intramuscularly) or by intramuscular injection. Therefore, for example, the compounds of the invention may be formulated with suitable polymeric or hydrophobic materials (for example, in the form of an emulsion in a suitable oil) or ionic exchange resins.

ALIAmides and Silymarin, derivatives thereof or conjugates or complexes thereof may be formulated in the same pharmaceutical composition or separately. For example, where an oral formulation is used for ALIAmides, also Silymarin could be formulated for a similar oral administration, or, alternatively, it could be administered in a different formulation, such as an injectable formulation or a suppository, and so on, according to the indications suggested by the clinician.

According to the present invention, the dose of an ALIAmide of the invention, or mixtures thereof, proposed for the administration to a human being (having a body weight of about 70 Kg) ranges from 1 mg to 2 g and, preferably, from 100 mg to 1 g of the active ingredient per dose unit; the dose of Silymarin, of derivatives thereof or conjugates or complexes thereof or mixtures thereof will, in turn, range between 1 mg and 2 g, or from 100 mg to 1 g, per dose unit, in which the dosage ration of ALIAmide and Silymarin, derivatives thereof or conjugates or complexes thereof, is as defined above. The dose unit may be administered, for example, 1 to 4 times a day. The dose will depend on the route selected for the administration. It shall be taken into account that it could be necessary to make continuous variations to the dosage, according to the age and weight of the patient, as well as the severity of the clinical condition to be treated. Finally, the exact dose and administration route will be at the discretion of the attending clinician o veterinary.

The pharmaceutical compositions of the invention will be able to be prepared by using conventional techniques, such as those described in Remington's Pharmaceutical Sciences Handbook, Mack Pub. Co., N.Y., USA, 17th edition, 1985.

Some non-limiting examples of pharmaceutical compositions according to the invention are set forth below.

EXAMPLES OF FORMULATIONS

Example No. 1

Tablets—Each Tablet Contains

| | |
|---|---|
| Micronized PEA | mg 50.00 |
| Silymarin | mg 400.00 |
| Microcrystalline cellulose | mg 80.00 |
| Sodium crosscaramellose | mg 44.00 |
| Polyvinylpyrrolidone | mg 10.00 |
| Magnesium stearate | mg 4.00 |
| Polysorbate 80 | mg 2.00 |

Example No. 2

Tablets—Each Tablet Contains

| | |
|---|---|
| Ultramicronized PEA | mg 70.00 |
| Silymarin | mg 500.00 |
| Microcrystalline cellulose | mg 120.00 |
| Sodium crosscaramellose | mg 60.00 |
| Polyvinylpyrrolidone | mg 15.00 |
| Magnesium stearate | mg 4.00 |
| Polysorbate 80 | mg 3.00 |

Example No. 3

Soft Gelatin Capsules—Each Capsule Contains

| | |
|---|---|
| PEA + Silymarin (1:10 w/w ratio) in co-ultramicronized form | mg 300.00 |
| Soy lecithin | mg 30.00 |
| Vegetable oil | mg 570.00 |

Example No. 4

Microgranules for Sub-Lingual Absorption each dose weighting 2.00 g microgranules contains:

| | |
|---|---|
| PEA + Silymarin (1:10 w/w ratio) in co-micronized form | mg 600.00 |
| Non-cariogenic sugars | mg 200.00 |
| Pharmacologically acceptable excipients | q.s. to g 2.00 |

What is claimed is:

1. A method of treatment of renal diseases comprising administering to a patient a combination of one or more compounds selected from amide of a C12-C20 monocarboxylic acid, saturated or monounsaturated, or a mono- or diamide of a C4-C14 dicarboxylic acid, saturated or monounsaturated, with an aminoalkanol, and of one or more compounds selected from Silymarin, analogs thereof or conjugates or complexes thereof, wherein said amide of a C12-C20 monocarboxylic acid, saturated or monounsaturated, or a mono- or diamide of a C4-C14 dicarboxylic acid, saturated or monounsaturated, with an aminoalkanol and said Silymarin, analogs thereof or conjugates or complexes thereof, are formulated for a separate, sequential, concomitant administration or in admixture.

2. The method according to claim 1, wherein said C12-C20 monocarboxylic acid, saturated or monounsaturated, is selected from palmitic acid, stearic acid, and oleic acid.

3. The method according to claim 1, wherein said C4-C14 dicarboxylic acid, saturated or monounsaturated, is selected from fumaric acid, azelaic acid, and trans-traumatic acid.

4. The method according to claim 1, wherein said compounds are palmitoylethanolamide and Silymarin.

5. The method according to claim 4, wherein said palmitoylethanolamide is in a micronized form.

6. The method according to claim 5, wherein at least 94% or at least 95% or about 96% of the particles of said micronized palmitoylethanolamide has a size of less than 10 microns and at least 77% or at least 78% or about 80% of the particles of said micronized palmitoylethanolamide has a size of less than 6 microns.

7. The method according to claim 4, wherein said palmitoylethanolamide is fully or partially in an ultra-micronized form.

8. The method according to claim 7, wherein at least 97% or at least 98% or at least 99% or about 99.9% of the particles of said palmitoylethanolamide ultra-micronized has dimensions of less than 6 microns and at least 57% or at least 58% or at least 59% or about 59.6% of the particles of said palmitoylethanolamide ultra-micronized has dimensions of less than 2 microns.

9. The method according to claim 1, wherein said Silymarin, analogs thereof or conjugates or complexes thereof are selected from total or partial extract of the plant *Silybum marianum*, Silibinin, Silibinin disodium dihydrogensuccinate, complex between Silymarin and phosphatidylcholine, inclusion complexes of Silymarin in β-cyclodextrins, hydroxypropyl-β-cyclodextrin and methylated β-cyclodextrin and Silibinin glycosides.

10. The method according to claim 1, wherein said compounds selected from Silymarin, analogs thereof or conjugates or complexes thereof are administered in a weight ratio ranging between 15:1 and 1:1, or between 10:1 and 5:1, with respect to said compounds selected from an amide of a C12-C20 monocarboxylic acid, saturated or monounsaturated, or a mono- or diamide of a C4-C14 dicarboxylic acid, saturated or monounsaturated, with an aminoalkanol.

11. The method according to claim 1, wherein said compounds selected from an amide of a C12-C20 monocarboxylic acid, saturated or monounsaturated, or a mono- or diamide of a C4-C14 dicarboxylic acid, saturated or monounsaturated, with an aminoalkanol and said compounds selected from Silymarin, analogs thereof or conjugates or complexes thereof are used in a co-micronized co-ultra-micronized form.

12. The method according to claim 1, wherein the renal diseases are caused by dysmetabolic diseases or toxic agents.

13. The method according to claim 1, wherein said renal diseases are selected from:
   Diabetic nephropathy
   Nephro-angio-sclerosis
   Pielonephritis
   Polycystic kidney disease (polycystic kidney)
   Alport's syndrome
   Lesch-Nyham's syndrome
   Goodpastures' syndrome
   Lupus nephritis
   Immunoglobulins A nephropathy
   Tubular necrosis
   Glomerulonephritis
   Urethral stenosis
   Iatrogenic nephropathies and nephropathies from NSADs, cytotoxic drugs, Lithium, antibiotics or Cyclosporine
   Nephropathies after radiation therapy
   Nephropathies in the elderly.

14. The method according to claim 1, wherein said compounds selected from an amide of a C12-C20 monocarboxylic acid, saturated or monounsaturated, or a mono- or diamide of a C4-C14 dicarboxylic acid, saturated or monounsaturated, with an aminoalkanol and said compounds selected from Silymarin, analogs thereof or conjugates or complexes thereof are contained in a same or separated pharmaceutical composition selected from tablets, capsules, granulates, solutions, syrups, suspensions, optionally with a controlled release, for oral administration; pills, tablets, or granulates for buccal or sub-lingual administration; suspensions, solutions or emulsions in oily or aqueous vehicles for injectable administration; suppositories or retention enema for rectal administration; depot preparation for subcutaneous, transcutaneous, or intramuscular administration, or for intramuscular injection.

15. The method according to claim 1, wherein the patient is a human.

16. The method according to claim 1, wherein the patient is an animal.

* * * * *